United States Patent
Yanagida et al.

(10) Patent No.: US 9,679,106 B2
(45) Date of Patent: Jun. 13, 2017

(54) MEDICAL INFORMATION DISPLAY APPARATUS

(71) Applicant: Toshiba Medical Systems Corporation, Otawara-shi (JP)

(72) Inventors: Yosuke Yanagida, Otawara (JP); Hiromasa Yamagishi, Otawara (JP); Yasunori Doi, Nasushiobara (JP)

(73) Assignee: Toshiba Medical Systems Corporation, Otwara-shi (JP)

( * ) Notice: Subject to any disclaimer, the term of this patent is extended or adjusted under 35 U.S.C. 154(b) by 79 days.

(21) Appl. No.: 14/632,478

(22) Filed: Feb. 26, 2015

(65) Prior Publication Data

US 2015/0243065 A1     Aug. 27, 2015

(30) Foreign Application Priority Data

Feb. 26, 2014  (JP) ................................ 2014-035187

(51) Int. Cl.
G06T 11/60    (2006.01)
G06F 19/00    (2011.01)
A61B 19/00    (2006.01)

(52) U.S. Cl.
CPC ........ *G06F 19/321* (2013.01); *G06F 19/3406* (2013.01); *G06T 2210/32* (2013.01); *G06T 2210/41* (2013.01)

(58) Field of Classification Search
CPC ............... G06F 19/321; G06F 19/3406; G06T 2210/32; G06T 2210/41
See application file for complete search history.

(56) References Cited

U.S. PATENT DOCUMENTS

| | | | |
|---|---|---|---|
| 2010/0114951 A1* | 5/2010 | Bauman | G06F 19/321 707/770 |
| 2011/0075901 A1* | 3/2011 | Nakamura | G06F 19/321 382/128 |
| 2012/0029939 A1* | 2/2012 | Danielson | G06F 19/322 705/3 |
| 2012/0159324 A1* | 6/2012 | Chavez | G06Q 50/24 715/704 |

FOREIGN PATENT DOCUMENTS

JP         4-49945        2/1992

* cited by examiner

*Primary Examiner* — Sing-Wai Wu
(74) *Attorney, Agent, or Firm* — Oblon, McClelland, Maier & Neustadt, L.L.P.

(57) ABSTRACT

A medical information display apparatus according to an embodiment includes: a displaying unit which displays medical information; a study information acquiring part which acquires study information; a to-be-started-app determining part which determines a starting-target application group from the study information acquired by the study information acquiring part; and a controlling unit which displays, on the displaying unit, a plurality of pieces of medical information created respectively by applications in the start target application group determined by the to-be-started-app determining part.

19 Claims, 4 Drawing Sheets

| PRIORITY | STUDY INFORMATION | | | TO-BE-STARTED APPLICATIONS |
|---|---|---|---|---|
| | MODALITY | BODY PART | CONTRAST ENHANCEMENT | |
| 1 | CT | HEAD | NO | App001,App002,App003 |
| 2 | CT | HEAD | YES | App004,App005,App006 |
| 3 | CT | CHEST | NO | App007,App008,App009 |
| 4 | CT | CHEST | YES | App010,App011,App012 |
| 5 | CT | STOMACH | * | App013,App014,App015 |
| 6 | CT | * | * | App016,App017,App018 |
| ⋮ | ⋮ | ⋮ | ⋮ | ⋮ |

| PRIORITY | App START SITUATION | | | | | STUDY INFORMATION | TO-BE-USED LAYOUT |
|---|---|---|---|---|---|---|---|
| | App001 | App002 | App003 | App004 | ·· App xxx | | |
| 1 | YES | YES | YES | NO | ·· NO | * | Layout001 |
| 2 | NO | YES | YES | YES | ·· NO | * | Layout002 |
| 3 | YES | YES | * | * | ·· * | * | Layout003 |
| 4 | | | | | ·· | * | Layout004 |
| 5 | | | | | ·· | * | Layout005 |
| 6 | | | | | ·· | * | Layout006 |
| ⋮ | ⋮ | ⋮ | ⋮ | ⋮ | ⋮ | ⋮ | ⋮ |

| TO-BE-USED LAYOUT | App | ARRANGEMENT | | | | |
|---|---|---|---|---|---|---|
| | | POSITION x | POSITION y | WIDTH | HEIGHT | STACKING ORDER (PRIORITY) |
| Layout001 | App001 | 0 | 0 | 1000 | 500 | 1 |
| Layout001 | App002 | 0 | 500 | 1000 | 500 | 2 |
| Layout001 | App003 | 1000 | 0 | 1000 | 1000 | 3 |
| Layout002 | App002 | 0 | 0 | 1000 | 500 | 1 |
| Layout002 | App003 | 0 | 500 | 1000 | 500 | 2 |
| Layout002 | App004 | 1000 | 0 | 1000 | 1000 | 3 |
| ⋮ | ⋮ | ⋮ | ⋮ | ⋮ | ⋮ | ⋮ |

MEDICAL INFORMATION DISPLAY APPARATUS

CROSS-REFERENCE TO THE RELATED APPLICATION

This application is based on and claims the benefit of priority from Japanese Patent Applications No. 2014-035187, filed on Feb. 26, 2014; the entire contents of which are incorporated herein by reference.

FIELD

Embodiments described herein relate generally to a medical information display apparatus.

BACKGROUND

In recent years, with the advancement of technology, medical image diagnosis apparatuses and systems using various electronic instruments have been installed in medical institutions. A medical image diagnosis apparatus is an apparatus which creates a medical image by collecting information on the inside of a subject and imaging the inside of the subject based on this collected information. Examples of such a medical image diagnosis apparatus include an X-ray computed tomography (CT) apparatus and a magnetic resonance imaging (MRI) apparatus.

Systems in the medical field have become diverse. When a user such as a radiographer or a radiologist in a hospital diagnoses the clinical condition of a patient by radiologically interpreting three-dimensional images captured with an X-ray CT apparatus or a magnetic resonance imaging apparatus, the user does such work by using applications of a plurality of systems such as a 2D viewer or a 3D viewer which performs volume rendering or three-dimensional maximum intensity projection (MIP) process, and clinical analysis application aimed at analyzing a particular body part or a particular illness.

Here, depending on the purpose of observation, the user sometimes changes the applications to be used and also the arrangements of medical images and reports on the monitors, and then compares these medical images, reports, or the like to perform radiological interpretation. In the case of radiological interpretation using a plurality of applications, the user starts a plurality of applications in accordance with the modality, the body part, and the purpose of the radiological interpretation, operates an input device such as a mouse to manually arrange a plurality of pieces of medical information (e.g. medical images or reports) created respectively by the applications to optimal, easily-viewable position positions, and then performs the radiological interpretation.

Note that it takes time for the user to manually change the display arrangement of each piece of medical information as described above, and the efficiency of radiological interpretation is therefore lowered. For example, assume that the user simultaneously starts a plurality of applications at the start of radiological interpretation. In this case, since the applications differ from each other in start time, the user needs to start all the applications and identify pieces of medical information created respectively by these applications in order to arrange the piece of medical information created respectively by each application to an optimal position. Thus, the user cannot perform radiological interpretation until all the applications are started and also until he or she finishes changing the arrangement of each piece of medical information. Accordingly, the efficiency of radiological interpretation is significantly lowered.

DETAILED DESCRIPTION

According to one embodiment, a medical information display apparatus includes: a displaying unit which displays medical information; a study information acquiring part which acquires study information; a to-be-started-app determining part which determines a starting-target application group from the study information acquired by the study information acquiring part; and a controlling unit which displays, on the displaying unit, a plurality of pieces of medical information created respectively by applications in the start target application group determined by the to-be-started-app determining part.

An embodiment will be explained with reference to the drawings.

Figure 1:
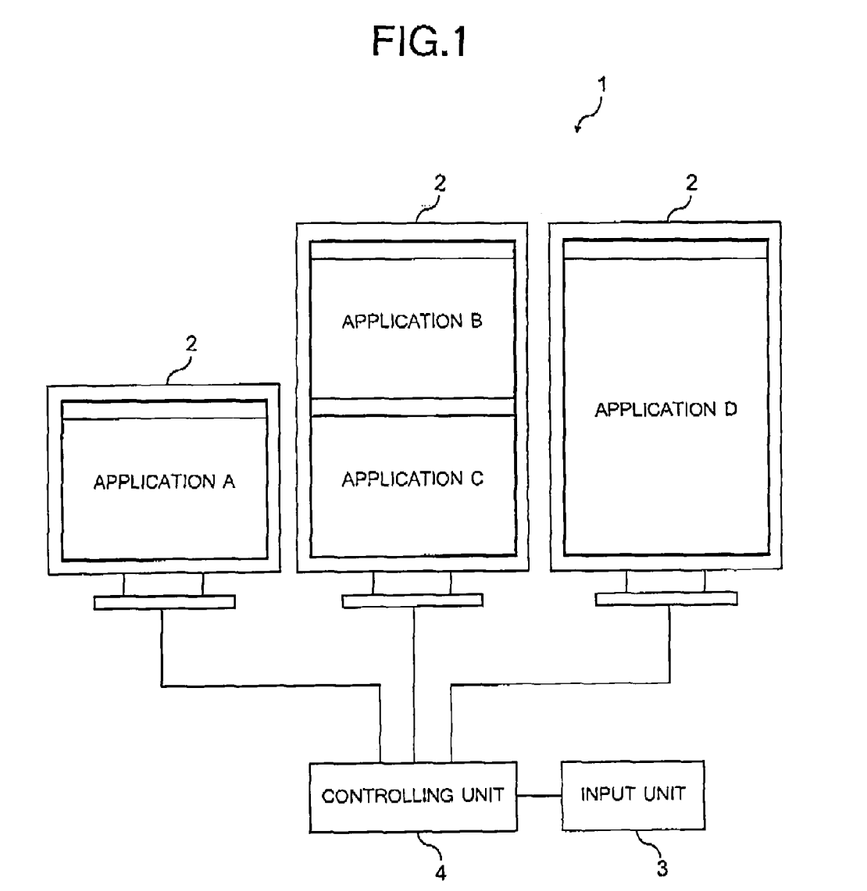
FIG. 1 is a diagram showing a schematic configuration of a medical information display apparatus according to an embodiment.

As shown in FIG. 1, a medical information display apparatus 1 according to an embodiment includes a plurality of displaying units 2 which display various kinds of medical information such as medical images and reports, an input unit 3 on which the user performs input operations, and a controlling unit 4 which controls given parts. This medical information display apparatus 1 serves as a terminal to be used by a user in a hospital such as a radiographer or a radiologist.

Each displaying unit 2 is a display device which displays various kinds of medical images such as CT images and MR images as well as report information such as radiological interpretation reports. A liquid crystal display, an organic electroluminescence (EL) display, a cathode ray tube (CRT) display, or the like is usable as the displaying unit 2, for example. Note that although three displaying units 2 are arranged side by side in FIG. 1, the number of displaying units and their layout are not limited to this example.

The input unit 3 is an operation unit which receives input operations from an operator such as a radiographer or a radiologist. Input devices such as a keyboard, a mouse, and a touchscreen are usable as this input unit 3, for example.

The controlling unit 4 is formed, for example, by a central processing unit (CPU), a read only memory (ROM), a random access memory (RAM), and the like, and controls given parts by loading and executing programs and the like based on input signals from the input unit 3. For example, the controlling unit 4 performs control to display, on the displaying units 2, various kinds of information such as data obtained by performing a predetermined process and data obtained by an application (hereinafter, abbreviated as "app" when appropriate).

Note that FIG. 1 shows an example in which medical information created by an application A is displayed on the left displaying unit 2 in the drawing, pieces of medical information created respectively by two applications B and C are displayed on the center displaying unit 2 in the drawing, and medical information created by an application D is displayed on the right displaying unit 2 in the drawing. Display arrangements as above are determined by a process, and the individual pieces of medical information (e.g. medical images and reports) are displayed on the plurality of displaying units 2 based on the display arrangements.

Here, as the applications A to D, a 2D display application (2D viewer), a 3D display application (3D viewer), a report making application, a clinical analysis (image analysis) application, and the like are available. These applications are provided by different companies, and the display specifications and the like differ from one company to another.

Figure 2:
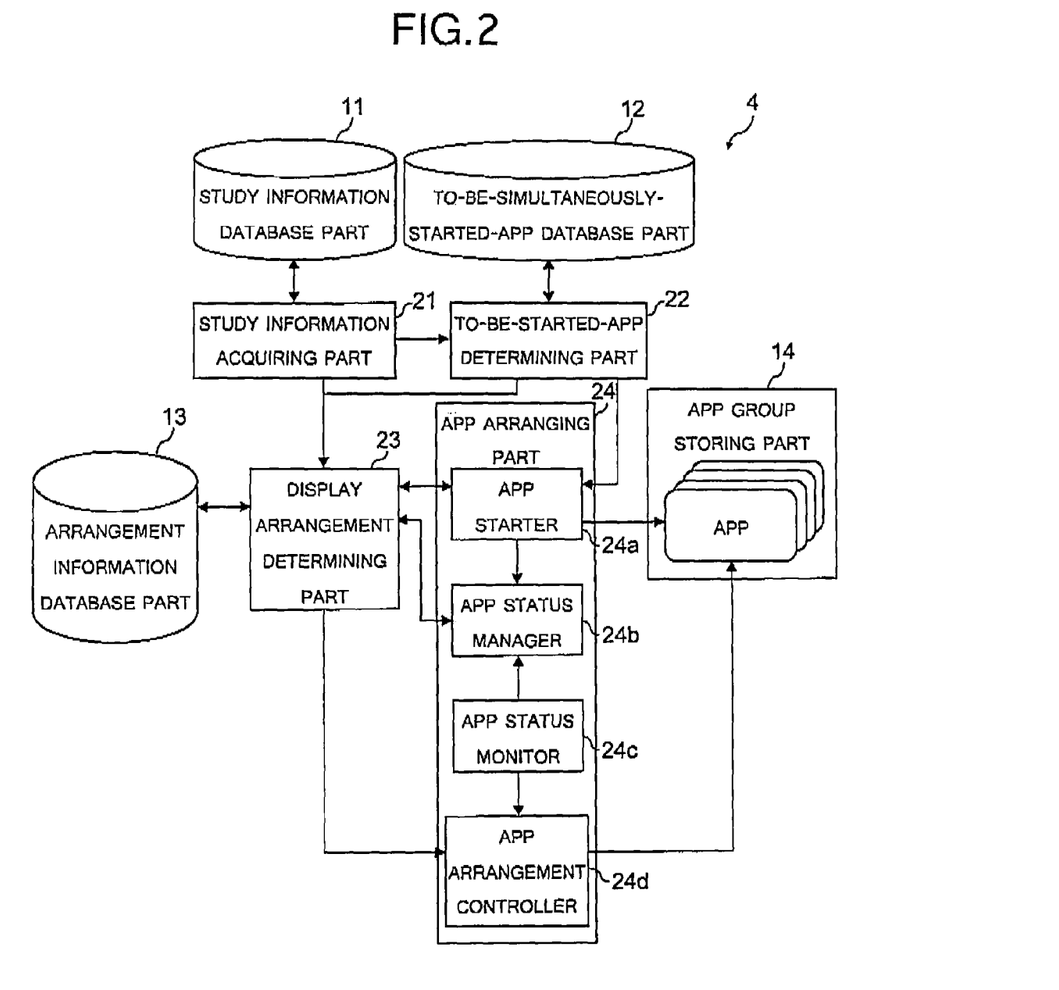
FIG. 2 is a block diagram showing a schematic configuration of a controlling unit included in the medical information display apparatus according to the embodiment.

Next, the controlling unit 4 mentioned above will be explained in detail.

As shown in FIG. 2, the controlling unit 4 includes: a study information database part 11 which stores and manages study information; a to-be-simultaneously-started-app database part 12 which stores and manages starting target applications to be started simultaneously; an arrangement information database part 13 which stores and manages arrangement information for determining display arrangements in accordance with which to display, on the displaying units 2, medical information such medical images and reports created by the applications; and an app group storing part 14 which stores a plurality of apps (app group).

The controlling unit 4 further includes: a study information acquiring part 21 which acquires study information from the study information database part 11; a to-be-started-app determining part 22 which determines applications to be started by using the to-be-simultaneously-started-app database part 12; a display arrangement determining part 23 which determines the optimal display arrangement for each piece of medical information by using the arrangement information database part 13; and an app arranging part 24 which starts applications and arranges pieces of medical information thereof. This app arranging part 24 includes: an app starter 24a which starts the applications to be started; an app status manager 24b which manages the start statuses of the applications; an app status monitor 24c which monitors the start statuses of the applications; and an app arrangement controller 24d which controls the arrangements of the pieces of medical information in accordance with the determined display arrangements.

The study information acquiring part 21 receives user specifying information which specifies the user, radiological interpretation-purpose specifying information which specifies the purpose of the radiological interpretation, study specifying information which specifies a study, and the like in response to the user's input operations on the input unit 3 (e.g. selecting a study) through an external application which allows the user to see a list of studies performed. Moreover, the study information acquiring part 21 uses these pieces of information to acquire information on the modality and body part corresponding to the selected study from the study information database part 11 and also acquires terminal environment information (such as the IP of the terminal and the number of displays) from the system information of the terminal. Thereafter, the study information acquiring part 21 transmits the user specifying information, the radiological interpretation-purpose specifying information, the modality information, the body part information, and the terminal environment information to the to-be-started-app determining part 22 and the display arrangement determining part 23.

The to-be-started-app determining part 22 searches the to-be-simultaneously-started-app database part 12 by using the user specifying information, the radiological interpretation-purpose specifying information, the modality information, the body part information, and the terminal environment information provided by the study information acquiring part 21, to thereby acquire a "to-be-started app group." Thereafter, the to-be-started-app determining part 22 transmits the "to-be-started app group" to the display arrangement determining part 23 and the app starter 24a.

The display arrangement determining part 23 acquires the user specifying information, the radiological interpretation-purpose specifying information, the modality information, the body part information, and the terminal environment information from the study information acquiring part 21. Moreover, the display arrangement determining part 23 acquires a "currently started app group" from the app status manager 24b (details will be described later) and also the "to-be-started app group" from the to-be-started-app determining part 22 and adds them together to obtain an "expected app group." Thereafter, the display arrangement determining part 23 searches the arrangement information database part 13 by using the user specifying information, the radiological interpretation-purpose specifying information, the modality information, the body part information, and the "expected app group" and determines the display position of medical information for each application in the "expected app group" (determination of the display arrangement of medical information). Here, the display position (display arrangement) of medical information means the coordinates of the start point of the application window, the height and width of the window, the order in which the window overlaps or is overlapped by other windows, and other similar information. Note that the arrangement information is stored, for example, as a template in the arrangement information database part 13 in association with the above-mentioned pieces of information in advance.

The app starter 24a acquires the "to-be-started app group" from the to-be-started-app determining part 22 and acquires the optimal display position (i.e. display arrangement) of medical information for each application from the display arrangement determining part 23. Thereafter, the app starter 24a performs a start process on each application included in the application group thus acquired. In this step, in the case where the application is an "application capable of being started with its display position designated at the time of the start," the app starter 24a designates the optimal display position of medical information of the application acquired from the display arrangement determining part 23 and instructs the application to start. On the other hand, in the case where the application is not an "application capable of being started with its display position designated at the time of the start," the app starter 24a simply instructs the application to start. Moreover, the app starter 24a notifies the app status manager 24b of start information indicating that applications have been started, and started application specifying information specifying the applications started. Here, the "application capable of being started with its display position designated at the time of the start" can be implemented such that the application itself inquires for its start position and starts at the optimal display position.

The app status manager 24b stores and updates the start status of each application and returns the start status upon request. Applications which are not started are managed as applications in a "non-started" state. In the case where the app starter 24a notifies that applications are started, the app status manager 24b shifts the state of each application in the "non-started" state to a "waiting-to-start" state. This "waiting-to-start" state refers to a state where the application is in the middle of a start process and has not yet been detected as being started by the app status monitor 24c. In the case where the app status monitor 24c notifies that the application is started, the app status manager 24b shifts its state to a "started" state. In the case where the app status monitor 24c notifies that the application is quitted, the app status manager 24b shifts its state to the "non-started" state. Moreover, in the case where the display arrangement determining part 23 inquires for the started applications, the app status manager 24b returns an application group which has been started. Here, the app status manager 24b returns applications in the "waiting-to-start" state also as applications in the "started" state.

The app status monitor 24c monitors the start statuses of the applications by continuously referring to windows displayed on the screens, i.e. a list of medical information. Moreover, in the case of detecting that an application is started or quitted, the app status monitor 24c notifies the app status manager 24b and the app arrangement controller 24d of application specifying information which specifies the application, and also notifies them that the application is started or quitted.

The app arrangement controller 24d acquires the optimal display arrangements determined by the display arrangement determining part 23. Moreover, the app arrangement controller 24d receives a notification of start of an application from the app status monitor 24c. Upon receipt of a notification of start, the app arrangement controller 24d forcibly arranges the medical information provided by the started application at the optimal display position in the case where the started application is not an "application capable of being started with its display position designated at the time of the start."

Note that the study information acquiring part 21, the to-be-started-app determining part 22, the display arrangement determining part 23, and the app arranging part 24 (the app starter 24a, the app status manager 24b, the app status monitor 24c, and the app arrangement controller 24d) described above may be configured by hardware such as electric circuits, by software such as programs which execute their functions, or by a combination of both.

Next, an explanation will be given of a case of simultaneously starting a plurality of applications E, F, and G, for example, in the medical information display apparatus 1 configured as described above, and displaying individual medical images created respectively by these applications E, F, and G on the display screen of one displaying unit 2. Note that like the applications A to D mentioned above, there are various kinds of applications available as the applications E to G.

The applications E, F, and G are determined as a "to-be-started app group" by using the user specifying information, the radiological interpretation-purpose specifying information, the modality information, the body part information, and the terminal environment information provided by the study information acquiring part 21 and searching the to-be-simultaneously-started-app database part 12 with the to-be-started-app determining part 22. Here, the start time of the application G which is the time taken to start the application G is longer than those of the other applications E and F.

Figure 3:
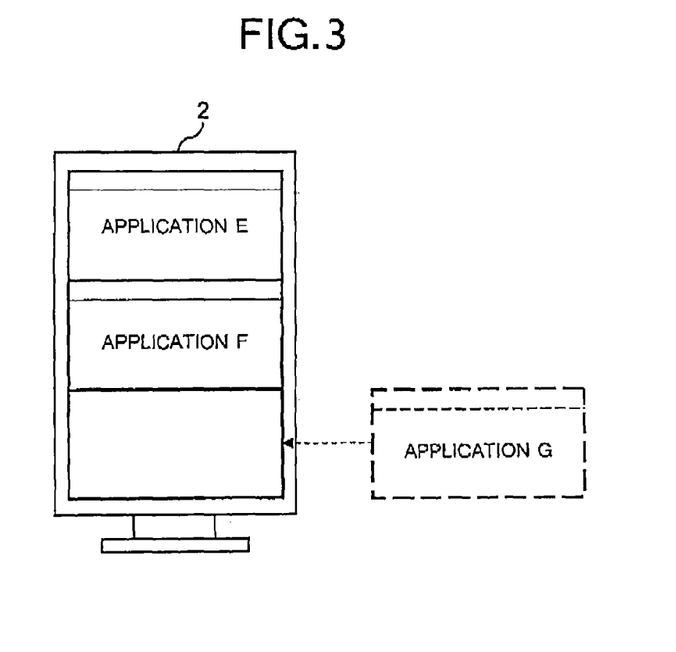
FIG. 3 is an explanatory diagram for explaining the display of medical information according to the embodiment.

For this reason, there is a situation as shown in FIG. 3 where the individual medical images created respectively by the applications E and F are displayed on the display screen of the displaying unit 2 in accordance with the display arrangements determined by the display arrangement determining part 23, whereas the medical image created by the application G is not yet displayed on the display screen of the displaying unit 2. Note that the predetermined display arrangements mentioned above, i.e. the coordinates of the start points of the application windows and the heights and widths of the windows are determined such that the application windows of the three applications E, F, and G can be arranged in an equal size within the display screen of the displaying unit 2 without overlapping each other.

Here, since the individual medical images created respectively by the applications E and F are displayed in accordance with the predetermined display arrangements mentioned above, the user does not need to wait to start radiological interpretation until the application G is started and its medical image is displayed, and can start radiological interpretation of the medical images currently displayed on the displaying unit 2. Even when the medical image created by the application G is then displayed on the display screen of the displaying unit 2, this medical image is displayed in accordance with its display arrangement mentioned above, so that the layouts of the medical images remain unchanged and the medical images are prevented from overlapping each other, for example. Accordingly, the user can smoothly continue the radiological interpretation of the medical images.

On the other hand, in the case where the display arrangements mentioned above are not determined in advance, the individual medical images created by the applications E and F are displayed on the display screen of the displaying unit 2 at given start positions (display positions at start) of the applications. This leads to a situation where the medical images may overlap each other or not be aligned, for example. In this case, the user needs to manually change the display arrangement of each piece of medical information to the optimal state, and time is needed for this change. Further, when the medical image obtained by the application G is displayed, the medical image is, too, displayed on the display screen of the displaying unit 2 at a given start position of the application G. Thus, the medical images may likewise overlap each other or not be aligned. In this case, too, the user needs to manually change the display arrangement of each piece of medical information to the optimal state, and time is needed for this change.

Here, in the case where the application is an "application capable of being started with its display position designated at the time of the start," the app starter 24a designates a start position corresponding to the display arrangement mentioned above and instructs the application to start. On the other hand, in the case where the application is not an "application capable of being started with its display position designated at the time of the start," the app arrangement controller 24d performs control which forcibly moves the medical image displayed at the given start position of the application to a display position corresponding to the display arrangement mentioned above (forcibly changing the display position).

As described above, the medical information display apparatus 1 performs control which involves: determining the application group the user needs and the final display arrangements defined by the application group prior to the start of the applications; and arranging the medical information of each application which is capable of being started with its display position designated, by designating the designating position and then starting the application, and arranging the medical information of each application which is not capable of being started with its display position designated, at the optimal display position immediately after its start. In this way, it is possible to start using those applications which are started, without waiting until those applications yet to be started are started or without waiting until the user finishes manually changing the display arrangements of the pieces of medical information. Accordingly, the time taken to start radiological interpretation can be reduced. Moreover, since the user no longer needs to manually change the display arrangements of the pieces of medical information, the user-friendliness is improved.

Next, a specific example of the process of determining the display arrangements (layout) of pieces of medical information (e.g. medical images and reports) will be explained with reference FIGS. 4 to 6.

Figure 4:
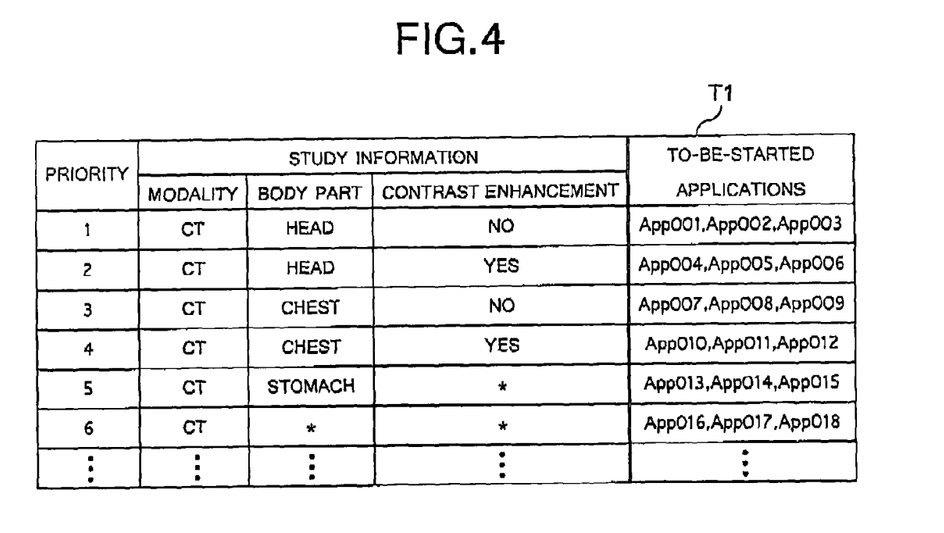
FIG. 4 is an example of a table for determining to-be-started applications based on study information according to the embodiment.

Prior to the process, a table T1 shown in FIG. 4 is stored in the to-be-simultaneously-started-app database part 12. This table T1 is an example of a table for determining the applications to be started (hereinafter, "to-be-started applications) based on study information. In the table T1, a set of to-be-used applications (to-be-started app group) is set for each combination of priority and study information (e.g. the type of modality, the body part, and use of contrast enhancement). Note that * symbols in FIG. 4 denote any characters (wildcards).

Figure 5:
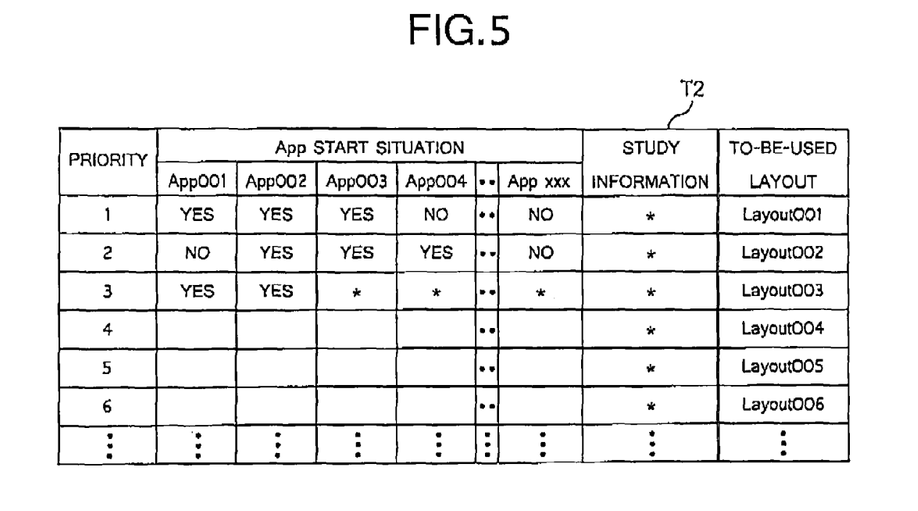
FIG. 5 is an example of a table for determining a to-be-used layout based on the to-be-started applications according to the embodiment.
Figure 6:
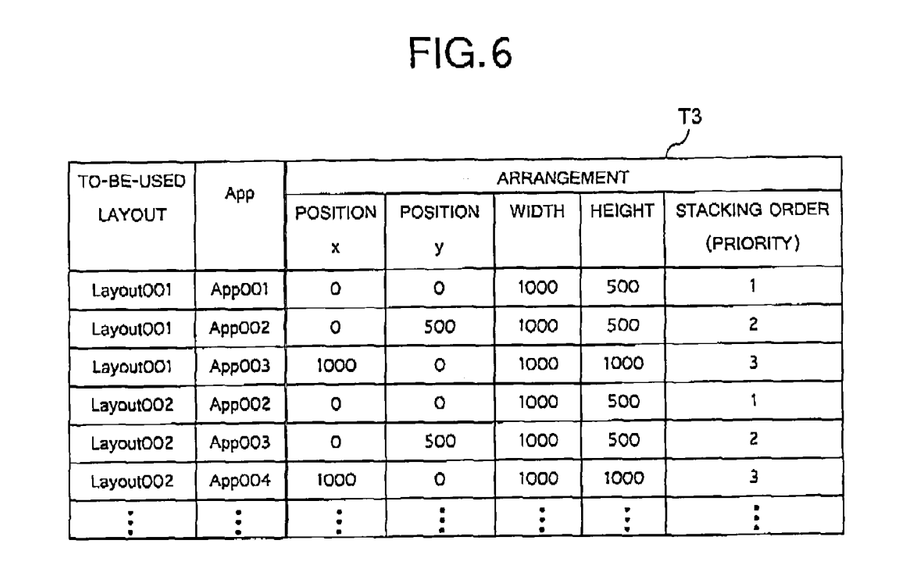
FIG. 6 is an example of a table for determining the arrangements of the applications based on the to-be-used layout according to the embodiment.

Moreover, a table T2 shown in FIG. 5 and a table T3 shown in FIG. 6 are stored in the arrangement information database part 13. The table T2 is an example of a table for determining the layout to be used (hereinafter, "to-be-used layout") based on the to-be-used applications. The table T3 is an example of a table for determining the arrangement of each application based on the to-be-used layout.

In the table T2, a to-be-used layout is set for each combination of priority, application start situation (App start situation), and study information. Moreover, in the table T3, an arrangement is set for each to-be-used layout and each application therein. Note that * symbols in FIG. 5 denote any characters (wildcards) like FIG. 4, the positions in FIG. 6 denote coordinates based on an origin, and the unit of the width and height in FIG. 6 is pixel.

The tables T1, T2, and T3 as described above are stored in advance. Upon input of study specifying information such as a study ID and a patient ID which specifies a study through the input unit 3, study information corresponding to this study specifying information is acquired by the study information acquiring part 21 from the study information database part 11. Then, to-be-started applications are determined which correspond to the acquired study information. In this step, as shown in FIG. 4, it is determined which study information in the table T1 the acquired study information matches, based on priority, that is, in descending order of priority (level of priority).

Here, in the case, for example, where the acquired study information indicates that the modality is CT, the body part is the head, and no contrast enhancement is used, App001, App002, and App003 are determined as the to-be-started applications as shown in FIG. 4. Likewise, in the case where the acquired study information indicates that the modality is CT, the body part is the head, and contrast enhancement is used, App004, App005, and App006 are determined as the to-be-started applications. Moreover, in the case where the acquired study information indicates that the modality is CT and the body part is the stomach, App013, App014, and App015 are determined as the to-be-started applications, irrespective of whether contrast enhancement is used or not (see the * symbol in FIG. 4).

Then, the to-be-started applications as determined above are used by the display arrangement determining part 23 to determine the to-be-used layout corresponding to the determined to-be-started applications. In this step, as shown in FIG. 5, it is determined which application start situation (App start situation) in the table T2 the determined to-be-started applications match, based on priority, that is, in descending order of priority (level of priority). Note that the study information in FIG. 5 has a * symbol for all cases and does not serve as a condition for determining the to-be-used layout. However, the study information will serve as a condition for determining the to-be-used layout if information (e.g. the type of modality, the body part, or whether or use of contrast enhancement) is inputted instead of the * symbol.

Here, in the case, for example, where the determined to-be-started applications are App001, App002, and App003, Layout001 is determined as the to-be-used layout as shown in FIG. 5. In the case where the to-be-used layout is Layout001 and one of the to-be-started applications is App001, the arrangement thereof is such that the position x is 0, the position y is 0, the width is 1000, the height is 500, and the stacking order (priority) is 1 as shown in FIG. 6. Likewise, in the case where the to-be-used layout is Layout001 and one of the to-be-started applications is App002, the arrangement thereof is such that the position x is 0, the position y is 500, the width is 1000, the height is 500, and the stacking order (priority) is 2. In the case where the to-be-used layout is Layout001 and one of the to-be-started applications is App003, the arrangement thereof is such that the position x is 1000, the position y is 0, the width is 1000, the height is 1000, and the stacking order (priority) is 3.

Note that the priority in stacking order means that when pieces of medical information overlap each other, one with higher priority is displayed on a nearer side. Thus, among App001, App002, and App003 in Layout001, the priority of App001 is the highest and the priority of App003 is the lowest.

As described above, a given arrangement is set for each to-be-started application in each to-be-used layout. Thus, in the case where Layout001 is determined as the to-be-used layout, medical information created by App001 is displayed in a predetermined size (1000×500) at predetermined coordinates (0, 0). Similarly, medical information created by App002 is displayed in a predetermined size (1000×500) at predetermined coordinates (0, 500). Further, medical information created by App003 is also displayed in a predetermined size (1000×1000) at predetermined coordinates (1000, 0).

As described above, the to-be-started applications are determined from the table T1 based on the study information, and the to-be-used layout is determined from the table T2 based on the to-be-started applications thus determined. Further, the display arrangement of medical information to be created by each to-be-started application (e.g. a medical image or report) is determined by using the arrangement of the to-be-started application from the table T3 based on the to-be-used layout thus determined. Then, the medical information is displayed on the displaying unit 2 based on the display arrangement thus determined.

As described above, the embodiment involves: determining a starting target application group from study information; determining display arrangements in accordance with which to display, on the displaying unit 2, a plurality of pieces of medical information (e.g. medical images or reports) created respectively by the applications in the starting target application group thus determined; and arranging the plurality of pieces of medical information created respectively by the applications in the starting target application group, by using the display arrangements thus determined. In this way, it is possible to start using applications which are started, without waiting until applications yet to be started are started or without waiting until the user finishes manually changing the display arrangements of the pieces of medical information. Thus, the time taken to start radiological observation can be shortened and the efficiency of radiological observation can be improved. Further, since the user no longer needs to manually change the display arrangements of the pieces of medical information, the user friendliness can be improved.

Moreover, by designating the start positions corresponding to the display arrangements mentioned above and instructing the application group to start, the pieces of medical information can be arranged securely and more easily in accordance with the display arrangements in the case where each of the applications is an "application capable of being started with its display position designated at the time of the start."

Moreover, the arrangements of the plurality of pieces of medical information created respectively by the applications in the starting target application group are controlled by using the above display arrangements and the start statuses of the applications in the starting target application group. In this way, even in the case where the applications are not "applications capable of being started with their display positions designated at the time of the start," the pieces of medical information thereof can be arranged securely and more easily in accordance with the above display arrangements.

Meanwhile, examples of systems built in a medical institution include a hospital information system (HIS), a radiological information system (RIS), a picture archiving communication system (PACS), a study system, and so on. It is unlikely that all those systems built in a medical institution are systems of a single vendor, though it depends on the scale of the medical institution to install the systems. This is because each vendor that develops a system(s) has their own area of specialty, and also because various applications are installed as applications to create medical information, such as an application that is good at X-ray image analysis and an application that is suitable for creating a 3D image from volume data obtained by an X-ray CT apparatus.

In the case where a plurality of systems and a plurality of applications are installed in a medical institution like the above case, these systems and applications operate in their own, non-uniform ways, thereby making themselves quite less friendly to the user (e.g. a doctor or a technician). Considering particularly the fact that various applications are installed in accordance with the preference, ability, and the like of the user who uses the applications, it is normal that the applications are provided not by a single system or vendor but by different systems or vendors. Image diagnosis, image observation, and the like are performed by using a plurality of applications of different systems for operations involving interpreting images, referring to images, and the like. According to the embodiment described above, even in the case where a plurality of applications of different systems or vendors (significantly different in start time) are used like the above case, it is possible to start using applications which are started, without waiting until applications yet to be started are started or until the user finishes manually changing the display arrangements of the pieces of medical information. Thus, the time taken to start radiological interpretation can be shortened and the efficiency of radiological interpretation can be improved.

For example, in the case of a tenant-type medical information system, a system administrator is positioned as the "landlord" while app providers that provide applications to be used are positioned as the "tenants." For this reason, in the tenant-type medical information system provided by the landlord, the tenants provide various applications and various app providers (various vendors) are present. The user obtains medical information he or she needs by using various applications provided by app providers which are tenants. Here, at present, the start times significantly differ between applications, especially between applications of different app providers. According to the embodiment described above, in such a case, too, it is possible to start using applications which are started, without waiting until applications yet to be started are started or without waiting until the user finishes manually changing the display arrangements of the pieces of medical information. Thus, the time taken to start radiological interpretation can be shortened and the efficiency of radiological interpretation can be improved.

Note that in the embodiment described above, pieces of medical information (e.g. medical images) are displayed on the displaying unit 2 without overlapping each other. Here, in the case, for example, where a piece of displaying target medical information is added due to start of a new application or by a similar event, the display arrangements (layout) of the plurality of pieces of medical information currently displayed may be changed such that the piece of medical information added and the plurality of pieces of medical information currently displayed can be displayed without overlapping each other. Moreover, in the case where some of the pieces of medical information currently displayed is deleted due to quit of the corresponding application which has been started or by a similar event, the display arrangements (layout) of the plurality of pieces of medical information currently displayed may be displayed by additionally using the display space of the deleted piece of medical information such that the medical images do not overlap each other. Note that the changing of the display arrangements described above includes rearranging the pieces of medical information, changing the sizes of the pieces of the medical information, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information display apparatus, comprising:
   a display configured to display medical information;
   study information acquiring circuitry configured to acquire study information;
   to-be-started-app determining circuitry configured to determine a starting target application group from the study information acquired by the study information acquiring circuitry; and controlling circuitry configured to determine a display arrangement and display, on the display, a plurality of pieces of medical information created respectively by applications in the starting target application group determined by the to-be-started-app determining circuitry, wherein the controlling circuitry determines a final display arrangement defined by the starting target application group prior to the start completion of the starting target application group determined by the to-be-started-app determining circuitry, and the controlling circuitry determines designation of a waiting-to-start state of an application in the starting target application group determined by the to-be-started-app determining circuitry.

2. The medical information display apparatus according to claim 1, wherein the controlling circuitry displays the plurality of pieces of medical information on the display such that the pieces of medical information do not overlap each other.

3. The medical information display apparatus according to claim 2, wherein the controlling circuitry includes:

display arrangement determining circuitry configured to determine the display arrangement in accordance with which to display, on the display, the plurality of pieces of medical information created respectively by the applications in the starting target application group; and app arranging circuitry configured to arrange the plurality of pieces of medical information by using the display arrangement determined by the display arrangement determining circuitry.

4. The medical information display apparatus according to claim 3, wherein the app arranging circuitry includes an app starter configured to designate start positions corresponding to the display arrangement and instructs the starting target application group to start.

5. The medical information display apparatus according to claim 3, wherein the app arranging circuitry includes:

an app status monitor configured to obtain a start status of each of the applications in the starting target application group; and an app arrangement controller configured to control arrangements of the plurality of pieces of medical information respectively created by the applications in the starting target application group, by using the display arrangement determined by the display arrangement determining circuitry and the start statuses of the applications in the starting target application group obtained by the app status monitor.

6. The medical information display apparatus according to claim 3, wherein the controlling circuitry changes arrangements of the plurality of pieces of medical information displayed on the display, in response to addition of a piece of medical information to be displayed on the display.

7. The medical information display apparatus according to claim 3, wherein in response to deletion of one or more of the pieces of medical information displayed on the display, the controlling circuitry changes arrangements of the remaining pieces of medical information displayed on the display.

8. The medical information display apparatus according to claim 2, wherein the controlling circuitry changes arrangements of the plurality of pieces of medical information displayed on the display, in response to addition of a piece of medical information to be displayed on the display.

9. The medical information display apparatus according to claim 2, wherein in response to deletion of one or more of the pieces of medical information displayed on the display, the controlling circuitry changes arrangements of the remaining pieces of medical information displayed on the display.

10. The medical information display apparatus according to claim 1, wherein the controlling circuitry includes:

display arrangement determining circuitry configured to determine the display arrangement in accordance with which to display, on the display, the plurality of pieces of medical information created respectively by the applications in the starting target application group; and app arranging circuitry configured to arrange the plurality of pieces of medical information by using the display arrangement determined by the display arrangement determining circuitry.

11. The medical information display apparatus according to claim 10, wherein the app arranging circuitry includes an app starter configured to designate start positions corresponding to the display arrangement and instructs the starting target application group to start.

12. The medical information display apparatus according to claim 11, wherein the controlling circuitry changes arrangements of the plurality of pieces of medical information displayed on the display, in response to addition of a piece of medical information to be displayed on the display.

13. The medical information display apparatus according to claim 11, wherein in response to deletion of one or more of the pieces of medical information displayed on the display, the controlling circuitry changes arrangements of the remaining pieces of medical information displayed on the display.

14. The medical information display apparatus according to claim 10, wherein the app arranging circuitry includes:

an app status monitor configured to obtain a start status of each of the applications in the starting target application group; and an app arrangement controller configured to control arrangements of the plurality of pieces of medical information respectively created by the applications in the starting target application group, by using the display arrangement determined by the display arrangement determining circuitry and the start statuses of the applications in the starting target application group obtained by the app status monitor.

15. The medical information display apparatus according to claim 14, wherein the controlling circuitry changes arrangements of the plurality of pieces of medical information displayed on the display, in response to addition of a piece of medical information to be displayed on the display.

16. The medical information display apparatus according to claim 14, wherein in response to deletion of one or more of the pieces of medical information displayed on the display, the controlling circuitry changes arrangements of the remaining pieces of medical information displayed on the display.

17. The medical information display apparatus according to claim 10, wherein the controlling circuitry changes arrangements of the plurality of pieces of medical information displayed on the display, in response to addition of a piece of medical information to be displayed on the display.

18. The medical information display apparatus according to claim 10, wherein in response to deletion of one or more of the pieces of medical information displayed on the display, the controlling circuitry changes arrangements of the remaining pieces of medical information displayed on the display.

19. A medical information display apparatus comprising:

a display configured to display medical information;

study information acquiring circuitry configured to acquire study information;

to-be-started-app determining circuitry configured to determine a starting target application group from the study information acquired by the study information acquiring circuitry; and controlling circuitry configured to determine a display arrangement and display, on the display, a plurality of pieces of medical information created respectively by applications in the starting target application group determined by the to-be-started-app determining circuitry, wherein the controlling circuitry determines designation of a waiting-to-start state of an application in the starting target application group determined by the to-be-started-app determining circuitry.

\* \* \* \* \*